United States Patent
Yang

(10) Patent No.: US 10,639,338 B2
(45) Date of Patent: May 5, 2020

(54) TRADITIONAL CHINESE MEDICINE COMPOSITION FOR TREATING PROSTATE CANCER, PREPARATION METHOD AND APPLICATION THEREOF

(71) Applicant: SHANGHAI ZHONGYAO BIO-TECHNOLOGY CO., LTD., Shanghai (CN)

(72) Inventor: Yihong Yang, Shanghai (CN)

(73) Assignee: SHANGHAI ZHONGYAO BIO-TECHNOLOGY CO., LTD., Shanghai (CN)

( * ) Notice: Subject to any disclaimer, the term of this patent is extended or adjusted under 35 U.S.C. 154(b) by 291 days.

(21) Appl. No.: 15/552,550

(22) PCT Filed: Jul. 20, 2016

(86) PCT No.: PCT/CN2016/090695
§ 371 (c)(1),
(2) Date: Aug. 22, 2017

(87) PCT Pub. No.: WO2017/024928
PCT Pub. Date: Feb. 16, 2017

(65) Prior Publication Data
US 2018/0050073 A1 Feb. 22, 2018

(30) Foreign Application Priority Data
Aug. 10, 2015 (CN) .......................... 2015 1 0487031

(51) Int. Cl.
| | | |
|---|---|---|
| A61K 36/00 | (2006.01) |
| A61K 36/074 | (2006.01) |
| A61K 36/53 | (2006.01) |
| A61P 35/00 | (2006.01) |
| A61K 31/7048 | (2006.01) |
| A61K 31/704 | (2006.01) |
| A61K 31/352 | (2006.01) |
| A61K 36/258 | (2006.01) |
| A61K 36/484 | (2006.01) |
| A61K 36/539 | (2006.01) |

(52) U.S. Cl.
CPC .......... *A61K 36/074* (2013.01); *A61K 31/352* (2013.01); *A61K 31/704* (2013.01); *A61K 31/7048* (2013.01); *A61K 36/258* (2013.01); *A61K 36/484* (2013.01); *A61K 36/53* (2013.01); *A61K 36/539* (2013.01); *A61P 35/00* (2018.01); *A61K 2236/33* (2013.01); *A61K 2236/331* (2013.01); *A61K 2236/333* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| CN | 1478537 A | | 3/2004 |
|---|---|---|---|
| CN | 1478538 A | * | 3/2004 |
| CN | 1478538 A | | 3/2004 |
| CN | 105106307 A | | 2/2015 |

* cited by examiner

*Primary Examiner* — Qiuwen Mi
(74) *Attorney, Agent, or Firm* — Fox Rothschild LLP

(57) ABSTRACT

The present invention relates to a traditional Chinese medicine composition for treating prostate cancer and its preparation method and application. The composition is prepared from *Ganoderma lucidum*, *Scutellaria baicalensis*, *Rabdosia rubescens*, *Panax notoginseng* and *Glycyrrhiza* as raw materials in a weight ratio of 2-3:1-2:1-2:0.5-1.5:0.5-1.5 and prepared by mixed extraction or object extraction. The present inventions simplifies the prescription of the composition, is conducive to quality control, and reduces production cost, while the product curative effect remains unaffected, thus has a good application prospect.

16 Claims, No Drawings

TRADITIONAL CHINESE MEDICINE COMPOSITION FOR TREATING PROSTATE CANCER, PREPARATION METHOD AND APPLICATION THEREOF

TECHNICAL FIELD

The present invention belongs to the field of prostate cancer treatment, in particular to a traditional Chinese medicine composition for treating prostate cancer, preparation method and application thereof.

BACKGROUND ART

Prostate cancer (PCA) is one of the most common malignancies in men. In the United States, prostate cancer has become a type of male cancer with the highest incidence, the mortality rate of which is second only to that of lung cancer. The incidence and mortality rate of prostate cancer in China also show a rapid upward trend year after year, thus research and drug development on prostate cancer has become one of the world's most popular topics.

Prostate cancer can be divided into sex hormone-dependent type and non-sex hormone-dependent type. The recurrence rate of a conventional method selected from laser irradiation from outside, radioactive substance implantation or radical surgery is high. For sex hormone-dependent prostate cancer, treatment of which is performed by administrating sex hormones, however, in most cases, the cancer will turn into a hormone-resistant type cancer; and side effects of chemotherapy drugs is large and its efficacy is not satisfactory. For non-sex hormone-dependent prostate cancer, there is no effective treatment currently. When patients are diagnosed with stage III or IV cancer, or prostate cancer recurrence and metastasis, a vast majority of patients can only wait for death. Therefore, there is a need for a treatment method with a small side effect and is easy to be performed, in other words, there is a need for a novel drug which have a small side effect, a high curative effect and a low cost. CN 103816258 discloses a traditional Chinese medicine composition for treating prostate cancer, which is prepared from the following raw materials in parts by weight: 50 to 70 parts of *Rhizoma panaois majoris*, 10 to 20 parts of *Ludwigia octovalvis*, 40 to 60 parts of *Eupolyphaga*, 10 to 20 parts of *Oldenlandia diffusa*, 15 to 25 parts of *Pleurotus albellus*, 15-25 parts of *Poria cocos*, 10-20 parts of Herb of Indian Pentanema, and 10-20 parts of *Glycyrrhiza*. However, those components actually have similar functions, and thus increasing the cost of production. CN1478538 discloses a traditional Chinese medicine composition for treating prostate cancer, in which *Folium isatidis*, *Dendranthema morifolium* and *Scutellaria baicalensis* have heat-clearing and detoxifying effect, and thus the similar effects are overlapped, and the production cost is increased.

SUMMARY

The technical problem to be solved by the present invention is to provide a traditional Chinese medicine composition for treating prostate cancer and its preparation method and application. The traditional Chinese medicine composition simplifies the prescription of the composition, is conducive to quality control, and reduces production cost, while the product curative effect remains unaffected, thus such composition has a good application prospect.

The traditional Chinese medicine composition for treating prostate cancer of the present invention is prepared from *Ganoderma lucidum, Scutellaria baicalensis, Rabdosia rubescens, Panax notoginseng* and *Glycyrrhiza* as raw materials in a weight ratio of 2-3:1-2:1-2:0.5-1.5:0.5-1.5.

The composition is prepared from *Ganoderma lucidum, Scutellaria baicalensis, Rabdosia rubescens, Panax notoginseng* and *Glycyrrhiza* as raw materials in a weight ratio of 2-3:1.5-2:1.5-2:1-1.5:1-1.5.

The composition is prepared from *Ganoderma lucidum, Scutellaria baicalensis, Rabdosia rubescens, Panax notoginseng* and *Glycyrrhiza* as raw materials in a weight ratio of 3:2:2:1:1.

The composition is prepared from *Ganoderma lucidum, Scutellaria baicalensis, Rabdosia rubescens, Panax notoginseng* and *Glycyrrhiza* as raw materials in a weight ratio of 2:1.5:2:1.5:1.

The traditional Chinese medicine composition is composed of alkaloid, polysaccharide, lactone, saponin, coumarin and total flavones extracted from the mixture of *Ganoderma lucidum, Scutellaria baicalensis, Rabdosia rubescens, Panax notoginseng* and *Glycyrrhiza* in the above weight ratio.

The traditional Chinese medicine composition is composed of *Ganoderma lucidum* polysaccharide, baicalin, oridonin, notoginsenoside, liquiritigenin and isoliquiritigenin extracted from *Ganoderma lucidum, Scutellaria baicalensis, Rabdosia rubescens, Panax notoginseng* and *Glycyrrhiza* respectively in the above weight ratio.

A method for preparing the traditional Chinese medicine composition for treating prostate cancer of the present invention comprises: the composition is prepared by mixing extraction method or object extraction method.

The mixing extraction method comprises the following steps:

(1) preparing raw materials: *Ganoderma lucidum, Scutellaria baicalensis, Rabdosia rubescens, Panax notoginseng* and *Glycyrrhiza* are crushed and mixed in a weight ratio of 2-3:1-2:1-2:0.5-1.5:0.5-1.5, and then the obtained traditional Chinese medicine mixture is divided into six equal parts;

(2) extraction of alkaloid:

i) one part of the traditional Chinese medicine mixture obtained in step (1) is lixiviated in several times or percolated with a 0.1% hydrochloric acid ethanol solution to obtain an acidic ethanol extract;

ii) the extract is concentrated under reduced pressure to give a concentrate;

iii) the concentrate is washed with acidic water (pH=4-5), and then filtrated to obtain a residue, and the residue is washed with acidic water to obtain an acidic aqueous solution;

iv) ammonia water is added to the acidic aqueous solution obtained in step iii) to form precipitate, which is filtered to obtain a precipitate of total alkaloids; or a) adding dilute acid to the acid aqueous solution obtained in step until pH=2 and extracting it with chloroform to obtain a chloroform layer and an aqueous layer; evaporating chloroform in the chloroform layer to obtain weak alkaloid;

b) adding base to the aqueous layer until pH=6-7, extracting it with chloroform to obtain an aqueous layer and a chloroform layer, evaporating chloroform in the chloroform layer to obtain strong alkaloid;

c) the aqueous layer obtained in the above b) is adjusted to pH 10 with a base and then extracted with butanol, and then butanol in the butanol layer is evaporated to give a water-soluble alkaloid;

d) combining the alkaloids obtained in the above a), b) and c) to obtain the total alkaloids;

(3) extraction of polysaccharide: one part of the mixture obtained in step (1) is extracted with hot water at 95-100° C., and the residue is discarded, after the filtrate is left for 12 hours, 50% or more of ethanol is added to the supernatant, and a precipitate of polysaccharide is obtained by centrifugation;

(4) extraction of lactone: one part of the traditional Chinese medicine mixture obtained in step (1) is refluxed with diethyl ether to remove pigment, and then recovering diethyl ether to obtain total lactone;

(5) extraction of saponin: one part of the traditional Chinese medicine mixture obtained in step (1) is refluxed with petroleum ether, followed by evaporating petroleum ether to obtain a degreased crude powder, which is extracted with 90-95% ethanol, the extract is then concentrated under reduced pressure to obtain a concentrated liquid;

a) the concentrated liquid is extracted with chloroform and ethanol in turn, and then chloroform and ethanol are recovered under reduced pressure to obtain crude total glycoside; or b) the concentrated liquid is extracted with butanol, and then butanol is recovered under reduced pressure to obtain crude saponin;

(6) extraction of coumarin: one part of the traditional Chinese medicine mixture obtained in step (1) is decocted by water for 1-2 hours, and then concentrating the decoction and adding concentrated hydrochloric acid to remove impurity of insoluble matter, the obtained clear liquor is placed to obtain crude crystals of coumarin;

(7) extraction of flavonoids: one part of the traditional Chinese medicine mixture obtained in step (1) is impregnated by 70-80% ethanol, and then ethanol in the ethanol solution is recovered under reduced pressure and the residue is dissolved in water and filtered to obtain an aqueous solution, the aqueous solution is extracted with ethyl acetate and then the ethyl acetate solution is concentrated under reduced pressure to obtain total flavonoids;

alkaloid, polysaccharide, lactone, saponin, coumarin and total flavonoids extracted in steps (2) to (7) are mixed to obtain the traditional Chinese medicine composition.

The object extraction method comprises the following steps:

(1) extraction of baicalin:

i) adding 10-15 times volume of water to the *Scutellaria baicalensis* component for boiling for 1-2 hours, and then filtering;

ii) the filtrate is adjusted to pH 1-2 with acid, kept at 80-90° C. for 30-40 minutes, and centrifuged to precipitate; the precipitate is stirred evenly with water, and the pH is adjusted to neutral by an addition of base, followed by an additional of 3-5 times volume of ethanol, and then filtering;

iii) adding acid to the filtrate to adjust pH to 1-2, stirring, followed by maintaining at 80-9011 for 30-40 minutes, and then filtering;

iv) washing the resulting precipitate with water, 50% ethanol and then washing or recrystallizing with 95% ethanol to obtain baicalin;

(2) extraction of notoginsenoside:

i) extracting the soluble fraction in the crude powder of the root of *Panax notoginseng* with methanol at a concentration below 50%, concentrating the methanol extract under reduced pressure, and then adding 3-5 times volume of water to the residue;

ii) the aqueous solution is extracted with diethyl ether, and then the aqueous layer is extracted with n-butanol, followed by evaporating to dryness under reduced pressure, and then subjected to silica gel column chromatography by eluting with $CHCl_3$, MeOH and $H_2O$ in 65:35:10 to obtain notoginsenoside;

(3) extraction of oridonin: extracting the dry powder of the leaf of *Rabdosia rubescens* with diethyl ether, discarding the residue, and then recovering diethyl ether in diethyl ether solution to obtain a green-brown residue; dissolving the residue in methanol, followed by decolorization to obtain clear methanol solution, which is concentrated under reduced pressure and then placed at room temperature overnight, and then subjected to filtration, evaporation of the methanol mother liquor, and grinding; eluting with diethyl ether, followed by crystallization; preferably, it is further adsorbed with neutral alumina, eluted with diethyl ether, and then crystallized;

(4) extraction of liquiritigenin and isoliquiritigenin: extracting *Glycyrrhiza* with 3-4 times volume of 90-95% ethanol, and then extracting the obtained ethanol solution by petroleum ether, followed by stirring and mixing the water layer into silica gel, then eluting with MeOH and $H_2O$ in 7:3, the eluate is concentrated to give a residue; water is added to the residue to completely dissolve it, and the solution is extracted with ethyl acetate, the ethyl acetate layer was extracted with 5% $Na_2CO_3$ aqueous solution, the aqueous sodium carbonate solution is adjusted with dilute acid to pH 5-6, and then extracted with ethyl acetate, the ethyl acetate solution is dried, and then separated by a polyamide column and eluted with a gradient of 10-90% ethanol in water to give liquiritigenin and isoliquiritigenin.

(5) *Ganoderma lucidum* polysaccharide containing *Ganoderma lucidum* glycopeptide and *Ganoderma lucidum*-β-D dextran (commercially available from Shanghai Agricultural Science Institute) is mixed with the active components extracted in the above steps (1) to (4) to obtain the traditional Chinese medicine composition.

Further comprising step (6):

a) the active ingredients obtained in steps (1) to (5) are pulverized to a fine powder of 200 microns or less;

b) crushing, drying the date/seaweed seed or sour pomegranate seed/dwarf pomegranate seed, extracting with 8 times volume of absolute ethanol, concentrating under reduced pressure and treating with potassium acetylide to obtain a powder;

c) mixing the substances obtained in a), b) in a weight ratio of 100 to 200:1.

Further comprising step d): charging the mixture obtained in c) into a capsule.

Use of the traditional Chinese medicine composition for treating prostate cancer of the present invention in preparing medicine for treating prostate cancer.

The present invention pays attention to the overall regulation of the human body, treats both manifestation and root cause of a disease, has certain curative effect on hormone-dependent and non-hormone-dependent prostate cancer, and has small toxicity and side effect; it can enhance efficacy and reduce adverse when combined with chemotherapy drugs for the treatment of prostate cancer reactions; for cancer patients subjected to postoperative radiotherapy and chemotherapy, it can significantly promote the recovery of normal body function; and for postoperative recurrence, it has a strong inhibition of cancer cell growth. The present invention can fill in the blank of traditional Chinese medicine preparation of prostatic cancer on the market and fill in the blank of the hormone-independent prostate cancer domestic drug, and can make up the insufficiency of global hormone-independent prostate cancer treating drug.

Beneficial Effect

The traditional Chinese medicine composition simplifies the prescription of the composition, is conducive to quality control, and reduces production cost, while the product curative effect remains unaffected, thus such composition has a good application prospect.

DETAILED DESCRIPTION

The invention will be further elucidated with reference to specific examples. It is to be understood that these examples are merely illustrative of the present invention and are not intended to limit the scope of the invention. It is also to be understood that various changes and modifications can be made to the invention by those skilled in the art upon reading of the teachings of the invention, equivalents of which fall within the scope of the claims appended thereto.

Example 1

(1) Preparing raw materials: *Ganoderma lucidum, Scutellaria baicalensis, Rabdosia rubescens, Panax notoginseng* and *Glycyrrhiza* are crushed and mixed in a weight of 3 kg, 2 kg, 2 kg, 1 kg and 1 kg. The obtained traditional Chinese medicine mixture is divided into six equal parts;
(2) extraction of alkaloids:
i) one part of the traditional Chinese medicine mixture obtained in step (1) is lixiviated in several times or percolated with a 0.1% hydrochloric acid ethanol solution to obtain an acidic ethanol extract;
ii) the extract is concentrated under reduced pressure to give a concentrate;
iii) the concentrate is washed with acidic water (pH=4-5), and then filtrated to obtain a residue, and the residue is washed with acidic water to obtain an acidic aqueous solution;
iv) ammonia water is added to the acidic aqueous solution obtained in step iii) to form precipitate, which is filtered to obtain a precipitate of total alkaloid; or
a) adding dilute acid to the acid aqueous solution obtained in step until pH=2 and extracting it with chloroform to obtain a chloroform layer and an aqueous layer; evaporating chloroform in the chloroform layer to obtain weak alkaloid;
b) adding base to the aqueous layer until pH=6-7, extracting it with chloroform to obtain an aqueous layer and a chloroform layer, evaporating chloroform in the chloroform layer to obtain strong alkaloid;
c) the aqueous layer obtained in the above b) is adjusted to pH 10 with a base and then extracted with butanol, and butanol in the butanol layer is evaporated to give a water-soluble alkaloid;
d) combining the alkaloids obtained in the above a), b) and c) to obtain total alkaloids; recovering the above chloroform and butanol for reuse of the extraction step; and drying the alkaloid residue at a low temperature and crystallizing it;
(3) extraction of polysaccharide: the crude powder of one part of the traditional Chinese medicine mixture obtained in step (1) is extracted with hot water at 95° C. for 2 h, and the residue is discarded. After the filtrate is left for 12 hours, 60% of ethanol is added to the supernatant, and a precipitate of polysaccharide is obtained by centrifugation; the precipitate of polysaccharide is then refined with ether.
(4) extraction of lactone: one part of the traditional Chinese medicine mixture obtained in step (1) is refluxed with diethyl ether to remove pigment, and then recovering diethyl ether to obtain total lactone;

(5) extraction of saponin: one part of the traditional Chinese medicine mixture obtained in step (1) is refluxed with petroleum ether, followed by evaporating petroleum ether to obtain a degreased crude powder, which is extracted with 95% ethanol, the extract is concentrated under reduced pressure to obtain a concentrated liquid;
a) the concentrated liquid is extracted with chloroform and ethanol in turn, and then chloroform and ethanol are recovered under reduced pressure to obtain crude total glycoside; or
b) the concentrated liquid is extracted with butanol, and then butanol is recovered under reduced pressure to obtain crude saponin;
(6) extraction of coumarin: one part of the traditional Chinese medicine mixture obtained in step (1) is decocted by water for 1 hours, and then concentrating the decoction and adding concentrated hydrochloric acid (30%) to remove impurity of insoluble matter, the obtained clear liquor is placed to obtain crude crystals of coumarin; after drying, the crystals are washed with acetone, dried, recrystallized with water, heated, filtered and decolored to obtain an aqueous solution, and after cooling, a pale yellow paste-like product of coumarin is obtained.
(7) extraction of flavonoids: one part of the traditional Chinese medicine mixture obtained in step (1) is impregnated by 70% ethanol, and then ethanol in the ethanol solution is recovered under reduced pressure and the residue is dissolved in water and filtered to obtain an aqueous solution. The aqueous solution is extracted with ethyl acetate and the ethyl acetate solution is concentrated under reduced pressure to obtain total flavonoids;
alkaloid, polysaccharide, lactone, saponin, coumarin and total flavonoids extracted in steps (2) to (7) are mixed to obtain the traditional Chinese medicine composition.

Example 2

(1) extraction of baicalin:
i) adding 10 times volume of water to 1.5 kg *Scutellaria baicalensis* for boiling for 1 hours, and then filtering;
ii) the filtrate is adjusted to pH 2 with acid, kept at 80° C. for 30 minutes, and centrifuged to precipitate; the precipitate is stirred evenly with water, and the pH is adjusted to neutral by an addition of base, followed by an additional of 5 times volume of ethanol, and then filtering;
iii) adding hydrochloric acid to the filtrate to adjust pH to 2, stirring, followed by maintaining at 80⍰ for 30 minutes, and then filtering;
iv) washing the resulting precipitate with water, 50% ethanol and then washing or recrystallizing with 95% ethanol to obtain baicalin;
(2) extraction of notoginsenoside:
i) extracting the soluble fraction in 1.5 kg crude powder of the root of *Panax notoginseng* with 40% methanol, concentrating the methanol extract under reduced pressure, and then adding 5 times volume of water to the residue;
ii) the aqueous solution is extracted with diethyl ether, and then the aqueous layer is extracted with n-butanol, followed by evaporating to dryness under reduced pressure, and then subjected to silica gel column chromatography by eluting with $CHCl_3$-MeOH—$H_2O$ in 65:35:10 to obtain notoginsenoside;
(3) extraction of oridonin: extracting 2 kg dry powder of the leaf of *Rabdosia rubescens* with diethyl ether, discarding the residue, and then recovering diethyl ether in diethyl ether solution to obtain green-brown residue; dissolving the residue in methanol, followed by decolorization to obtain clear methanol solution, which is concentrated under reduced pressure and then placed at room temperature overnight, and then subjected to filtration, evaporation of the methanol mother liquor, and grinding; it is then further adsorbed with neutral alumina, eluted with diethyl ether, and then crystallized;

(4) extraction of liquiritigenin and isoliquiritigenin: extracting 1 kg *Glycyrrhiza* with 3 times volume of 95% ethanol, and then extracting the obtained ethanol solution by petroleum ether, followed by eluting the water layer through silica gel with MeOH—$H_2O$ in a volume ratio of 7:3, the eluate is concentrated to give a residue; water is added to the residue to completely dissolve it, and the solution is extracted with ethyl acetate, the ethyl acetate layer is extracted with 5% $Na_2CO_3$ aqueous solution, and the aqueous sodium carbonate solution is adjusted with dilute hydrochloric acid to pH 5-6, and then extracted with ethyl acetate, the ethyl acetate solution is dried, followed by being separated by a 60-mesh polyamide column and eluted with a gradient of 10-90% ethanol in water to give liquiritigenin and isoliquiritigenin;

(5) *Ganoderma lucidum* polysaccharide containing *Ganoderma lucidum* glycopeptide and *Ganoderma lucidum*-β-D dextran (its amount equivalent to the 2 kg of raw materials of the *Ganoderma lucidum*, Shanghai Agricultural Science Institute) is mixed with the active components extracted in the above steps (1) to (4) to obtain the traditional Chinese medicine composition.

The traditional Chinese medicine composition (1) is pulverized to a fine powder (2) of 200 microns or less; crushing, drying the date/seaweed seed (PHOENIXDACTYLIFERAL), extracting with 8 times volume of absolute ethanol, the extraction is preferably carried out three times, and the filtrate is combined, concentrating under reduced pressure and treating with potassium acetylide to obtain a powder (3); mixing fine powder (2) and powder (3) in a weight ratio of 100 to 200:1, charging the mixture obtained into a capsule to obtain capsules of the traditional Chinese medicine composition of the present invention.

In order to show the therapeutic effect of the traditional Chinese medicine composition of the present invention on prostate cancer, 8 patients were treated with the traditional Chinese medicine composition prepared in Example 1 with the following effects:

TABLE 1

Effect of the traditional Chinese medicine composition of the present invention on 8 patients

| Age | PSA before administration of the traditional Chinese medicine composition of the present invention | PSA after administration of the traditional Chinese medicine composition of the present invention |
|---|---|---|
| 70 | 128 | 62 (3 weeks) |
| 65 | 154 | 78 (4 weeks) |
| 73 | 87 | 7 (1 week) |
| 76 | 136 | 43 (8 weeks) |
| 55 | 40 | 15 (2 months) |
| 68 | 10 | 3.6 (4 months) |
| 75 | 188 | 81 (5 weeks) |
| 60 | 65 | 9.8 (2 weeks) |

Note:
PSA is an important specific antigen index of prostate cancer; PSA changes can explain the changes of prostate cancer.

It can be seen from the above results that the PSA index of all the patients suffering from prostate cancer is decreased after administration the traditional Chinese medicine composition of the present invention, that is, the traditional Chinese medicine composition of the present invention has a therapeutic effect on prostate cancer. For all patients, quality of life is improved, appetite is increased, and energy becomes strong.

In another clinical trial, the traditional Chinese medicine composition of the present invention prepared in Example 2 is effective after administration in all six sex hormone-dependent prostate cancer patients. In 6 cases of non-sex hormone-dependent prostate cancer, the effective rate reaches 75% after administration of the traditional Chinese medicine composition of the present invention prepared in Example 2. See Table 2 specifically.

TABLE 2

Effect of 12 patients taking the traditional Chinese medicine composition of the present invention

| | Condition | Age | PSA before administration of the traditional Chinese medicine composition of the present invention | PSA after administration of the traditional Chinese medicine composition of the present invention |
|---|---|---|---|---|
| 1 | Sex | 68 | 112 | 56 (2 weeks) |
| 2 | hormone- | 69 | 160 | 78 (3 weeks) |
| 3 | dependent | 78 | 86 | 30 (2 weeks) |
| 4 | prostate | 74 | 136 | 43 (3 weeks) |
| 5 | cancer | 53 | 50 | 13 (3 months) |
| 6 | | 81 | 20 | 11.4 (2 months) |
| 7 | Non-sex | 55 | 120 | 81 (5 weeks) |
| 8 | hormone- | 60 | 65 | 64 (3 weeks) |
| 9 | dependent | 58 | 143 | 68 (3 weeks) |
| 10 | prostate | 70 | 80 | 12 (2 weeks) |
| 11 | cancer | 74 | 97 | 50 (1 months) |
| 12 | | 79 | 130 | 42 (2 months) |

The invention claimed is:

1. A traditional Chinese medicine composition for treating prostate cancer, characterized by: the composition is prepared from raw materials consisting of *Ganoderma lucidum, Scutellaria baicalensis, Rabdosia rubescens, Panax notoginseng* and *Glycyrrhiza* in a weight ratio of 2-3:1-2:1-2:0.5-1.5:0.5-1.5.

2. The traditional Chinese medicine composition for treating prostate cancer according to claim 1, characterized by: the composition is prepared from raw materials consisting of *Ganoderma lucidum, Scutellaria baicalensis, Rabdosia rubescens, Panax notoginseng* and *Glycyrrhiza* in a weight ratio of 2-3:1.5-2:1.5-2:1-1.5:1-1.5.

3. The traditional Chinese medicine composition for treating prostate cancer according to claim 2, characterized by: the composition is prepared from raw materials consisting of *Ganoderma lucidum, Scutellaria baicalensis, Rabdosia rubescens, Panax notoginseng* and *Glycyrrhiza* in a weight ratio of 3:2:2:1:1.

4. The traditional Chinese medicine composition for treating prostate cancer according to claim 2, characterized by: the composition is prepared from raw materials consisting of *Ganoderma lucidum, Scutellaria baicalensis, Rabdosia rubescens, Panax notoginseng* and *Glycyrrhiza* in a weight ratio of 2:1.5:2:1.5:1.

5. The traditional Chinese medicine composition for treating prostate cancer according to claim 1, characterized by: the traditional Chinese medicine composition is composed of alkaloid, polysaccharide, lactone, saponin, coumarin and total flavones extracted from the mixture of *Ganoderma lucidum, Scutellaria baicalensis, Rabdosia rubescens, Panax notoginseng* and *Glycyrrhiza*.

6. The traditional Chinese medicine composition for treating prostate cancer according to claim 2, characterized by: the traditional Chinese medicine composition is composed of alkaloid, polysaccharide, lactone, saponin, coumarin and total flavones extracted from the mixture of *Ganoderma lucidum, Scutellaria baicalensis, Rabdosia rubescens, Panax notoginseng* and *Glycyrrhiza*.

7. The traditional Chinese medicine composition for treating prostate cancer according to claim 3, characterized by: the traditional Chinese medicine composition is composed of alkaloid, polysaccharide, lactone, saponin, coumarin and total flavones extracted from the mixture of *Ganoderma lucidum, Scutellaria baicalensis, Rabdosia rubescens, Panax notoginseng* and *Glycyrrhiza*.

8. The traditional Chinese medicine composition for treating prostate cancer according to claim 4, characterized by: the traditional Chinese medicine composition is composed of alkaloid, polysaccharide, lactone, saponin, coumarin and total flavones extracted from the mixture of *Ganoderma lucidum, Scutellaria baicalensis, Rabdosia rubescens, Panax notoginseng* and *Glycyrrhiza*.

9. The traditional Chinese medicine composition for treating prostate cancer according to claim 1, characterized by: the traditional Chinese medicine composition is composed of *Ganoderma lucidum* polysaccharide, baicalin, oridonin, notoginsenoside, liquiritigenin and isoliquiritigenin extracted from *Ganoderma lucidum, Scutellaria baicalensis, Rabdosia rubescens, Panax notoginseng* and *Glycyrrhiza* respectively.

10. The traditional Chinese medicine composition for treating prostate cancer according to claim 2, characterized by: the traditional Chinese medicine composition is composed of *Ganoderma lucidum* polysaccharide, baicalin, oridonin, notoginsenoside, liquiritigenin and isoliquiritigenin extracted from *Ganoderma lucidum, Scutellaria baicalensis, Rabdosia rubescens, Panax notoginseng* and *Glycyrrhiza* respectively.

11. The traditional Chinese medicine composition for treating prostate cancer according to claim 3, characterized by: the traditional Chinese medicine composition is composed of *Ganoderma lucidum* polysaccharide, baicalin, oridonin, notoginsenoside, liquiritigenin and isoliquiritigenin extracted from *Ganoderma lucidum, Scutellaria baicalensis, Rabdosia rubescens, Panax notoginseng* and *Glycyrrhiza* respectively.

12. The traditional Chinese medicine composition for treating prostate cancer according to claim 4, characterized by: the traditional Chinese medicine composition is composed of *Ganoderma lucidum* polysaccharide, baicalin, oridonin, notoginsenoside, liquiritigenin and isoliquiritigenin extracted from *Ganoderma lucidum, Scutellaria baicalensis, Rabdosia rubescens, Panax notoginseng* and *Glycyrrhiza* respectively.

13. A method for preparing the traditional Chinese medicine composition for treating prostate cancer according to claim 1 comprises: the composition is prepared by mixing extraction method or object extraction method.

14. The method for preparing the traditional Chinese medicine composition for treating prostate cancer according to claim 13, characterized by: the mixing extraction method comprises the following steps:
   (1) preparing raw materials: *Ganoderma lucidum, Scutellaria baicalensis, Rabdosia rubescens, Panax notoginseng* and *Glycyrrhiza* are crushed and mixed in a weight ratio of 2-3:1-2:1-2:0.5-1.5:0.5-1.5, and then the obtained traditional Chinese medicine mixture is divided into six equal parts;
   (2) extraction of alkaloid:
      i) one part of the traditional Chinese medicine mixture obtained in step (1) is lixiviated in several times or percolated with a 0.1% hydrochloric acid ethanol solution to obtain an acidic ethanol extract;
      ii) the extract is concentrated under reduced pressure to give a concentrate;
      iii) the concentrate is washed with acidic water, and then filtrated to obtain a residue, and the residue is washed with acidic water to obtain an acidic aqueous solution;
      iv) ammonia water is added to the acidic aqueous solution obtained in step iii) to form precipitate, which is filtered to obtain the total alkaloid precipitate; or
      a) adding dilute acid to the acid aqueous solution obtained in step iii) until pH=2 and extracting it with chloroform to obtain a chloroform layer and an aqueous layer; evaporating chloroform in the chloroform layer to obtain weak alkaloid;
      b) adding base to the aqueous layer until pH=6-7, extracting it with chloroform to obtain an aqueous layer and a chloroform layer, evaporating chloroform in the chloroform layer to obtain strong alkaloid;
      c) the aqueous layer obtained in the above b) is adjusted to pH 10 with a base and then extracted with butanol, and then butanol in the butanol layer is evaporated to give a water-soluble alkaloid;
      d) combining the alkaloids obtained in the above a), b) and c) to obtain total alkaloids;
   (3) extraction of polysaccharide: one part of the traditional Chinese medicine mixture obtained in step (1) is extracted with hot water at 95-100° C., and the residue is discarded, after the filtrate is left for 12 hours to obtain a supernatant, 50% or more of ethanol is added to the supernatant, and a polysaccharide precipitate is obtained by centrifugation;
   (4) extraction of lactone: one part of the traditional Chinese medicine mixture obtained in step (1) is refluxed with diethyl ether to remove pigment, and then recovering diethyl ether to obtain total lactone;
   (5) extraction of saponin: one part of the traditional Chinese medicine mixture obtained in step (1) is refluxed with petroleum ether, followed by evaporating petroleum ether to obtain a degreased crude powder, which is extracted with 90-95% ethanol, the extract is then concentrated under reduced pressure to obtain a concentrated liquid;
      a) the concentrated liquid is extracted with chloroform and ethanol in turn, and then chloroform and ethanol are recovered under reduced pressure to obtain crude total glycoside which includes saponin glycoside; or
      b) the concentrated liquid is extracted with butanol, and then butanol is recovered under reduced pressure to obtain crude saponin;
   (6) extraction of coumarin: one part of the traditional Chinese medicine mixture obtained in step (1) is decocted by water for 1-2 hours, and then concentrating the decoction and adding concentrated hydrochloric acid to remove impurity of insoluble matter, the obtained clear liquor is then placed to obtain crude crystals of coumarin;
   (7) extraction of flavonoids: one part of the traditional Chinese medicine mixture obtained in step (1) is impregnated by 70-80% ethanol, and then ethanol in the ethanol solution is recovered under reduced pressure and the residue is dissolved in water and filtered to obtain an aqueous solution; the aqueous solution is extracted with ethyl acetate and the ethyl acetate solution is concentrated under reduced pressure to obtain total flavonoids;

alkaloid, polysaccharide, lactone, saponin, coumarin and total flavonoids extracted in steps (2) to (7) are mixed to obtain the traditional Chinese medicine composition.

15. The method for preparing the traditional Chinese medicine composition for treating prostate cancer according to claim 13, characterized by: the object extraction method comprises the following steps:
   (1) extraction of baicalin:
   i) adding 10-15 times volume of water to the *Scutellaria baicalensis* component for boiling for 1-2 hours, and then filtering;
   ii) the filtrate is adjusted to pH 1-2 with acid, kept at 80-90° C. for 30-40 minutes, and centrifuged to precipitate; the precipitate is stirred evenly with water, and the pH is adjusted to neutral by an addition of base, followed by an additional of 3-5 times volume of ethanol, and then filtering;
   iii) adding acid to the filtrate to adjust pH to 1-2, stirring, followed by maintaining at 80-90° C. for 30-40 minutes, and then filtering;
   iv) washing the resulting precipitate with water, 50% ethanol and then washing or recrystallizing with 95% ethanol to obtain baicalin;
   (2) extraction of notoginsenoside:
   i) extracting crude powder of the root of *Panax notoginseng* with methanol at a concentration below 50%, concentrating the methanol extract under reduced pressure, and then adding 3-5 times volume of water to the residue;
   ii) the aqueous solution is extracted with diethyl ether, and then the aqueous layer is extracted with n-butanol, followed by evaporating to dryness under reduced pressure, and then subjected to silica gel column chromatography by eluting with $CHCl_3$, MeOH and $H_2O$ in 65:35:10 to obtain notoginsenoside;
   (3) extraction of oridonin: extracting the dry powder of the leaf of *Rabdosia rubescens* with diethyl ether, discarding the residue, and then recovering diethyl ether in diethyl ether solution to obtain green-brown residue; dissolving the residue in methanol, followed by decolorization to obtain clear methanol solution, which is concentrated under reduced pressure and then placed at room temperature overnight, and then subjected to filtration, evaporation of the methanol mother liquor, and grinding; eluting with diethyl ether, followed by crystallization;
   (4) extraction of liquiritigenin and isoliquiritigenin: extracting *Glycyrrhiza* with 3-4 times volume of 90-95% ethanol, and then extracting the obtained ethanol solution by petroleum ether, followed by stirring and mixing the water layer into silica gel, then eluting with MeOH and $H_2O$ in 7:3, the eluate is concentrated to give a residue; water is added to the residue to completely dissolve it, and the solution is extracted with ethyl acetate, the ethyl acetate layer is extracted with 5% $Na_2CO_3$ aqueous solution, and the aqueous sodium carbonate solution is adjusted with dilute acid to pH 5-6, and then extracted with ethyl acetate, the ethyl acetate solution is dried, followed by being separated by a polyamide column and eluted with a gradient of 10-90% ethanol in water to give liquiritigenin and isoliquiritigenin;
   (5) *Ganoderma lucidum* polysaccharide containing *Ganoderma lucidum* glycopeptide and *Ganoderma lucidum*-β-D dextran is mixed with the active components extracted in the above steps (1) to (4) to obtain the traditional Chinese medicine composition.

16. A method for treating prostate cancer by using the traditional Chinese medicine composition for treating prostate cancer according to claim 1.

\* \* \* \* \*